United States Patent [19]

Charm et al.

[11] Patent Number: 5,200,311
[45] Date of Patent: Apr. 6, 1993

[54] METHOD OF DETERMINATION OF PESTICIDES BY RADIOBIOCHEMISTRY

[75] Inventors: Stanley E. Charm, Boston; Shlomo Capua, Winchester; Eliezer Zomer, Quincy, all of Mass.

[73] Assignee: Charm Sciences Inc., Malden, Mass.

[21] Appl. No.: 556,952

[22] Filed: Jul. 19, 1990

[51] Int. Cl.$^5$ ............ C12Q 1/00; C12Q 1/18; G01N 1/00; G01N 33/564
[52] U.S. Cl. ............................ 435/4; 435/32; 436/504; 436/804; 424/2
[58] Field of Search ............ 435/4, 32; 436/504, 436/804; 424/2

[56] References Cited

U.S. PATENT DOCUMENTS

| | | | |
|---|---|---|---|
| 3,408,259 | 10/1968 | Krüger et al. | 435/4 |
| 4,238,472 | 12/1980 | Albro et al. | 436/540 |
| 4,469,795 | 9/1984 | Ginns et al. | 436/504 |
| 4,520,112 | 5/1985 | Snyder et al. | 436/504 |
| 4,925,664 | 5/1990 | Jackson et al. | 424/537 |
| 5,064,657 | 11/1991 | Jackson et al. | 424/537 |

OTHER PUBLICATIONS

Navarro et al., Journal of Chromatography, 138, pp. 423-429, 1977.
Guilbault, G. G. and Kramer, D. N. (1965), anal. Chem., 34:120.
Guilbault, G. G., Kuan, J., Moore, W. and Lozes, R. (1972), Environ. Letters, 3:300.
Guilbault, G. G., Sadar, M., Kuan, S., Casey, D. (1970), Anal. Chim. Acta, 52:75.
Guilbault, G. G., Kuan, S. and Sadar, M. (1970), Anal. Chem., 42:1770.
Guilbault, G. G., Kuan, S. and Sadar, M. (1970), J. Agr. Food Chem., 18:692.
Guilbault, G. G., Kuan, S. and Sadar, M. (1970), Anal. Chim. Acta, 51:83.
Giang, P. A. and Hall, S. A. (1951), Anal. Chem., 23:1830.
Archer, T. E. and Zweig, G. (1958), J. Agr. Food Chem., 6:910.

Primary Examiner—Douglas W. Robinson
Assistant Examiner—Deborah K. Ware
Attorney, Agent, or Firm—Richard P. Crowley

[57] ABSTRACT

A biochemical system in the determination of pesticides which is able to detect and measure the presence of parts per billion levels of different pesticides particularly in foodstuffs. The method employs insect tissues that contain specific binders or enzymes sensitive to various groups of pesticides. The sample or sample extract containing pesticides, radiolabeled pesticides and/or radiolabeled pesticide analogs and/or radiolabeled substrates is exposed to insect tissues containing receptors or enzymes. The pesticide competes with the radioactive tracers for the binders or the enzymes in the insect tissues. Residual enzyme activity or bound pesticides are measured. The extent of binding or enzyme activity may be inversely proportional, under standardized conditions, to the amount of pesticide in the sample.

10 Claims, 1 Drawing Sheet

METHOD OF DETERMINATION OF PESTICIDES BY RADIOBIOCHEMISTRY

BACKGROUND OF THE INVENTION

Different kinds of organisms (arthropods, avians, mammals) are sensitive to pesticides. Pesticides interact with their nervous and enzymatic systems. Such toxicants may bind to binders (ion channels) located on the nerve cells, or to enzymes located around them and elsewhere. Pesticides also interact with various protective mechanisms, such as degrading enzymes and non-specific binders.

Pesticides are generally classified as herbicides, fungicides and insecticides. It is desirable to test for the concentration of pesticides in various materials, particularly foodstuffs, for health and safety purposes. In particularly, it is desirable to provide an effective test method to determine the concentration level of organophosphorus and carbamate pesticides at low levels, such as below 50 ppb. Specific organophosphorus insecticides may be tested for pesticides employing antibodies, but not at low pesticide levels. Herbicides may be tested on a specific basis by chromogenic enzyme-based test methods, but such tests do not provide accurate results at low levels and are susceptible to color interpretation.

Therefore, a new, accurate, effective test method and kit for the determination of organophosphorus and carbamate pesticides, particularly in foodstuffs, are desirable.

SUMMARY OF THE INVENTION

The invention relates to a method and test kit for the determination of pesticides. In particular, the invention concerns a test method and test kit for the determination of organophosphorus and carbamate-type pesticides at levels below about 50 ppb in foodstuffs.

The method for detecting pesticides employs organisms, such as avian and insect tissues as a bag of receptors or enzymes, that interact with pesticides. The amount of radiolabeled pesticides, pesticide analogs or substrates, specifically interacting with the receptors or enzyme activity, is measured. This interaction is affected by the presence of the sampled pesticides and is inversely proportional to their amount. Two approaches, namely the use of binders or enzymes, were examined and shown to be effective for measuring pesticides. The enzyme activity method is more sensitive than the receptor binding method.

The invention comprises a method for the determination of the concentration of a material, such as a pesticide, and more particularly, an organophosphorus or carbamate-type pesticide in any test material, but particularly in foodstuffs at a low concentration level, such as below 50 ppb or even below 10 ppb or 5 ppb to ppt. The method is a radioassay-type method which includes adding a selected amount of an organic tissue material from an organism which is sensitive to the pesticide and which organic tissue material may comprise, for example, material selected from avian or insect tissues, such as for example, brain tissues of chicks or insects, like bees or houseflies. The organic tissue material should contain binding receptors or enzymes, or a combination, that interact with the pesticide which is to be determined in the test sample. The method includes incubating the test sample and the organic tissue material together, and thereafter adding a radiolabeled substrate which is selected to interact with the binding receptors or interact with the enzymes or the organic tissue material. The radiolabeled substrate may vary when it is particularly a [14-C]type substrate, such as for example, but not limited to: a naphthol salt, such as naphthyl acetate. The mixture is then incubated, typically at 37° C. for 40 minutes or more, for example, 40 to 80 minutes, to provide an interacted mixture of the organic tissue material, the test sample for which the pesticide level is to be determined and the radiolabeled substrate material. The resulting interacted mixtures are then separated to provide a desired liquid test sample. The separation may occur in a variety of ways. For example, the separation may be by chromatographic separation wherein the organic tissue material contains an enzyme, or by ultrafiltration or other filtration of membrane technique for organic tissue material which contain binding receptors. Optionally and typically, though, the elevant or filtrate from the separation process is then shaken in a scintillation fluid added to the material and the radioactivity of the separated fraction with the scintillation fluid therein is then determined by measuring the counts per minute. The level of concentration of the pesticide in the test sample is then determined by comparing the radioactivity of the tested fraction with that of a standard control sample, such as for example, a standard control curve of counts per unit time vs concentration previously prepared for the pesticide.

A. MATERIALS

The components used to determine and measure the presence of pesticides are: (1) receptors and/or enzymes which interact with pesticides; (2) radiolabeled substrates, pesticides and pesticide analogs; (3) non-radiolabeled standard grade pesticides; (4) separation units; and (5) buffers (reaction buffers, separation buffers).

B. METHODS

1. Receptors/Enzymes

Different organisms may serve for the preparation of receptors/enzymes. Binding assays are performed, for example, with chick brain homogenates. One gram of chick brain is homogenized in 8 ml of cold (4° C.) sodium phosphate buffer (50 mM pH 6.7) with Tissumizer ™ (Tekmar) for 30 seconds at 9500 rpm. Enzymatic assays are done with house fly (*Musca domestica*) brain tissue. Twenty-five heads are homogenized in 1 ml of cold (4° C.) sodium phosphate buffer (50 mM, pH 6.7) in a glass/teflon homogenizer. Homogenates are centrifuged in a clinical centrifuge at 1600 g for 10 minutes. The chick brain supernatant is diluted in the above buffer and used for binding assays. The house fly supernatant is loaded on a pre-equilibrated, disposable chromatography column (New Econo-Pac ™ 10, Bio-Rad). Equilibration is done with sodium phosphate buffer 50 mM, pH 6.7. The same cold buffer is used to elute the enzymes from the column. The first 3 ml are discarded. The next 5 ml are pooled together and serve as the enzyme source. They are kept in small aliquots at −70° C. until used. Before being used, the enzymes are thawed out and diluted appropriately in sodium phosphate buffer (50 mM, pH 6.7).

2. Standard Pesticide Solutions

Different concentrations of standard graded pesticides are prepared in acetone (high pressure liquid chromatography—HPLC grade).

3. Radiolabeled Substrate

[14-C] naphthyl acetate is synthesized. Residues of [14-C] naphthol are removed by HPLC. The substrate is kept at −70° C. until used.

4. The Assay

Five milliliters aliquots of sodium phosphate buffer 50 mM, pH 6.7, or free of pesticide samples (water, juice, milk, etc.) are spiked with known amounts of a pesticide. These solutions serve as positive controls. The receptors are added to the solutions in the appropriate concentration. Background solutions are assayed without receptors. The background, spiked and suspected (unknown) solutions are incubated for 20 minutes at 37° C. The radiolabeled substrate is added, and the solutions are incubated at 37° C. for 40 more minutes. The incubation is terminated by loading the solutions on C-8 disposable chromatography columns (Bond-Elut TM, Analytichem International). The columns are washed with water (2×5 ml), ethanol 10% (3×2 ml) and then eluted by 1 ml aliquots of an elution buffer (ammonium acetate 0.1M pH 8.2, containing 20% acetonitrile and 20% methanol).

The fractions containing [14-C] naphthol are pooled together, and a sample of 400–600 microliters is mixed with 4 ml of scintillation liquid (Ultima-Gold TM, Packard). The radioactivity (counts per minute—cpm) of the background assay (solutions assayed without receptors) is subtracted from all the other measurements. The results related to the spiked and suspected solutions are subtracted from those related to the zero-spiked solution (negative control). The inhibition standard curve is obtained by plotting results of the positive control assays (Y axis) vs. the corresponding concentrations (X axis).

Binding assays are performed by incubation of a diluted chick brain preparation (1:8) with [14-C] parathion (48.000 cpm). The incubation is done in the presence or absence of 10 ppm non-radiolabeled parathion at 45° C. for 20 minutes. Parathion molecules bound to the homogenate are separated from the free ones by a pre-equilibrated, disposable chromatography column (New Econo-Pac TM 10, Bio-Rad). The separation is achieved by following the same procedure used for purification of house fly enzymes. Fractions No. 3–6 correspond to the bound parathion. These fractions are pooled together, and the amount of bound [14-C] parathion is quantified.

A wide variety of organism tissue material can be used in the assay method of the invention, such as but not limited to:

| Anthropods | Avians | Mammals |
|---|---|---|
| Bees | Pigeon | Human |
| Beetles | | Bovine |
| Aphids | | Rat |
| Mosquitoes | | Mouse |
| Mites | | |

The invention will be described for the purposes of illustration only in connection with certain illustrated embodiments; however, it is recognized that those persons skilled in the art may make various improvements, additions, changes and modifications to the illustrated embodiments all falling within the spirit and scope of the invention.

DESCRIPTION OF THE EMBODIMENTS

Figure 1:
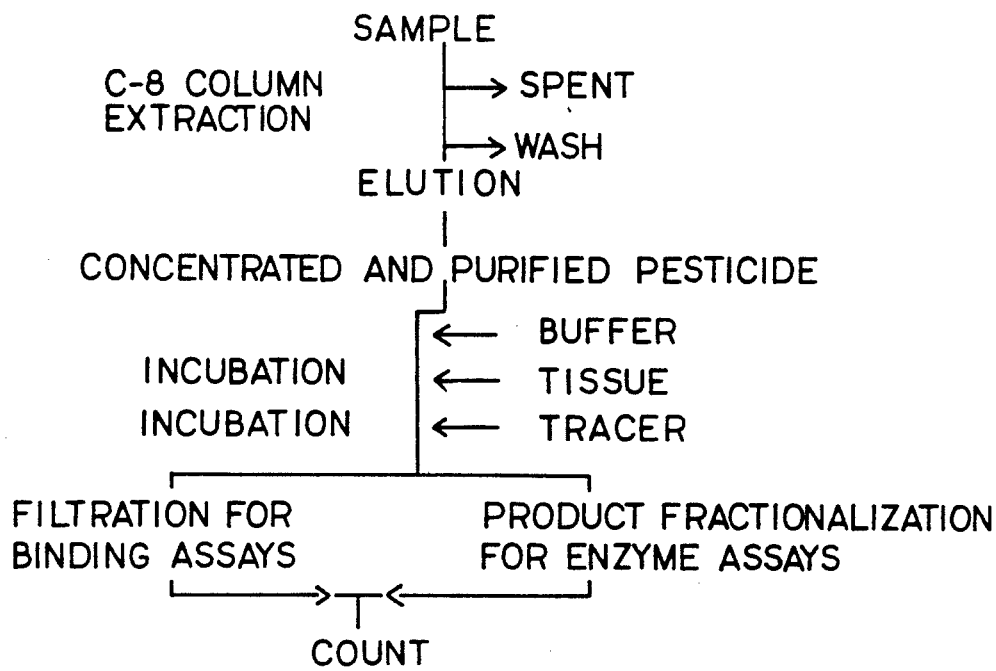
FIG. 1 is a schematic representation of the test method of the invention.
Figure 2:
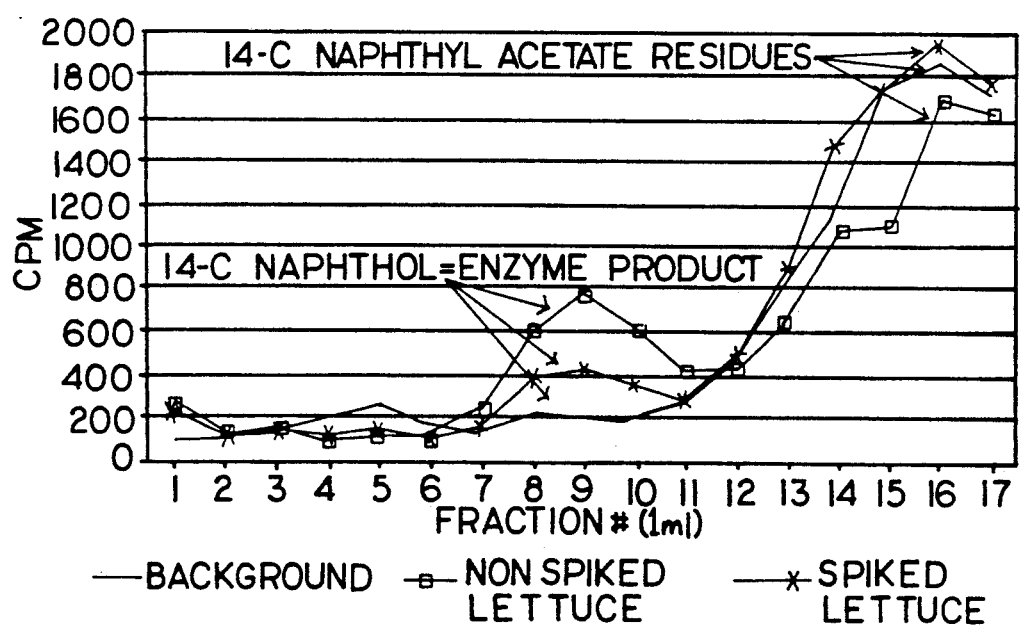
FIG. 2 is a graphical illustration of the determination of a pesticide in lettuce showing counts per minute (cpm) vs. fractions collected in milliliters.

A schematic representation of the method is illustrated in FIG. 1. The presence of 10 ppm of non-radiolabeled parathion reduced the binding rate of 41% (fractions 4+5).

FIG. 3 is a graphical illustration of test data from the determination of the organophosphorus pesticide parathion in lettuce employing an enzymatic source housefly homogenate. The test data graphically illustrated shows that the enzymatic assay method of the invention is able to detect the pesticide parathion in lettuce to 7 ppm. The test assay monitored this enzymatic product which is the radiolabled [14-C] naphthol which is enzymatically cleaved from the added parent compound [14-C] naphthyl acetate. The presence of the organophosphorus pesticide reduces the enzymatic activity of the housefly homogenate, and therefore, the amount of the cleaved product. As shown, the amount of the product (cpm) is determined vs. the chromatographic fraction collected. The illustrated data shows the background, the non-spiked lettuce and the spiked lettuce. The pesticide was detected as shown at 7 ppm which reduced the enzymatic activity by 63%.

In summary, the method employs a relatively crude tissue preparation which contains a battery of several types of esterolytic enzymes (in addition to acetylcholine esterase) and/or receptors sensitive to different pesticides, and the use of radiolabeled compounds enhances the sensitivity and accuracy of the assays.

REFERENCES

1. Guilbault, G. G. and Kramer, D. N. (1965), *Anal. Chem.*, 34: 120.
2. Guilbault, G. G., Kaun, J., Moore, W. and Lozes, R. (1972), *Environ. Letters*, 3: 300.
3. Guilbault, G. G., Sadar, M., Kuan, S., Casey, D. (1970), *Anal. Chim. Acta*, 52: 75.
4. Guilbault, G. G., Kaun, S. and Sadar, M. (1970), *Anal. Chem.*, 42: 1770.
5. Guilbault, G. G., Kaun, S. and Sadar, M. (1970), *J. Agr. Food Chem.*, 18: 692.
6. Guilbault, G. G., Kaun, S. and Sadar, M. (1970), *Anal. Chim. Acta*, 51: 83.
7. Giang, P. A. and Hall, S. A. (1951), *Anal. Chem.*, 23: 1830.
8. Archer, T. E. and Zweig, G. (1958), *J. Agr. Food Chem.* 6: 910.

TABLE 1

| Compound | Receptor Dilution | Pesticide Concentration (ppb) | CPM | Inhibition (%) |
|---|---|---|---|---|
| ORGANOPHOSPHATES | | | | |
| Parathion | 1:650 | 0 | 3443 | — |
| | | 100 | 2643 | 23 |
| | | 250 | 2661 | 23 |
| | | 500 | 2616 | 24 |
| Diazinon | 1:1100 | 0 | 2070 | — |
| | | 25 | 2080 | 0 |
| | | 50 | 2140 | 0 |
| | | 100 | 1320 | 36 |
| Chlorpyrifos | 1:1100 | 0 | 1930 | — |

TABLE 1-continued

| Compound | Receptor Dilution | Pesticide Concentration (ppb) | CPM | Inhibition (%) |
|---|---|---|---|---|
| | | 25 | 450 | 77 |
| | | 50 | 320 | 83 |
| | | 100 | 20 | 99 |
| Dichlorovos | 1:1100 | 0 | 2030 | — |
| | | 25 | 0 | 100 |
| | | 50 | 0 | 100 |
| | | 100 | 0 | 100 |
| CARBAMATES | | | | |
| Aldicarb | 1:900 | 0 | 2897 | — |
| | | 25 | 2523 | 13 |
| | | 50 | 2303 | 21 |
| | | 100 | 2095 | 28 |
| Carbofuran | 1:1100 | 0 | 2716 | — |
| | | 25 | 425 | 84 |
| | | 50 | 433 | 84 |
| | | 100 | 675 | 75 |
| Methomyl | 1:1100 | 0 | 2208 | — |
| | | 25 | 2308 | 0 |
| | | 50 | 1741 | 21 |
| | | 100 | 925 | 58 |
| Propoxur | 1:1100 | 0 | 2617 | — |
| | | 25 | 1425 | 45 |
| | | 50 | 867 | 67 |

What is claimed is:

1. A method for a radioactive assay for the determination of the concentration of an organophosphorus or carbamate pesticide in a test sample from a food product at concentration levels of below about 50 ppb, which method comprises:
   a) adding to a food test sample a selected amount of an insect brain tissue material homogenate, which tissue material contains binding receptors or enzymes that interact with the pesticide to be tested in the test sample;
   b) incubating the test sample and the tissue material;
   c) adding a $C^{14}$ radiolabeled pesticide the same as the pesticide to be tested and which interacts with the binding receptors and enzymes of the tissue material; d) incubating the test sample with the tissue material and the $C^{14}$ radiolabeled pesticide to provide an interacted mixture;
   e) separating the interacted mixture into a liquid fraction comprising the interacted test sample, tissue material and $C^{14}$ radioactive pesticide;
   f) adding a scintillation material to the liquid fraction;
   g) determining the counts per minute of the liquid fraction; and
   h) comparing the counts per minute of the separated fraction with the counts per minute from a standard control chart to determine the concentration of the pesticide in the test sample, the concentration of the pesticide in the test sample being about 50 ppb or less.

2. A radioactive assay method for the determination of the concentration of an organophosphorus or carbamate pesticide in a test sample from a food product at concentration levels of below about 50 ppb, which method comprises:
   a) admixing the test sample with a selected amount of insect brain tissue material, which tissue material contains binding receptors or enzymes that interact with the pesticide to be determined in the test sample;
   b) incubating the admixture;
   c) adding a $C^{14}$ radiolabeled compound to the incubated admixture, which $C^{14}$ radiolabeled compound interacts with the binding receptors or enzymes of the brain tissue of the incubated admixture;
   d) incubating the $C^{14}$ radiolabeled compound and the admixture to obtain a $C^{14}$ reacted admixture;
   e) separating the $C^{14}$ reacted mixture to obtain a liquid fraction comprising the interactive test sample, brain tissue and $C^{14}$ radiolabeled compound;
   f) determining the amount of radioactivity of the separated liquid fraction; and
   g) comparing the determined amount of radioactivity of the separated fraction with a standard control range of radioactivity to determine the concentration of the organophosphorus or carbamate pesticide in the test sample.

3. The method of claim 2 wherein the organic tissue material is *Musca domestica* brain tissue homogenate.

4. The method of claim 2 wherein the $C^{14}$ radiolabeled compound comprises a naphthol salt.

5. The method of claim 2 wherein the $C^{14}$ radiolabled compound comprises a $C^{14}$ radiolabled pesticide whose concentration is to be determined.

6. The method of claim 2 which includes separating the $C^{14}$ reacted mixture by chromatographic separation to obtain an eluant liquid fraction.

7. The method of claim 2 which includes separating the $C^{14}$ reacted mixture by ultrafiltration to obtain a filtrate liquid fraction.

8. The method of claim 2 which includes adding a scintillation liquid to the liquid fraction and determining the radioactivity of the liquid fraction by measuring the counts per minute.

9. The method of claim 2 wherein the $C^{14}$ reactive compound is $C^{14}$ naphthyl acetate.

10. The method of claim 2 wherein the insect brain tissue comprises a homogenate derived from flies, bees, beetle, aphids, mosquitoes and mites.

* * * * *